United States Patent [19]

Iovanni

[11] Patent Number: 5,217,652

[45] Date of Patent: Jun. 8, 1993

[54] CONDITIONING SHAMPOO

[75] Inventor: Carl F. Iovanni, Quincy, Mass.

[73] Assignee: The Gillette Company, Boston, Mass.

[21] Appl. No.: 771,598

[22] Filed: Oct. 4, 1991

[51] Int. Cl.$^5$ .................. C11D 1/00; C11D 7/00; A61K 7/00

[52] U.S. Cl. .................. 252/547; 252/548; 252/549; 252/550; 252/174.15; 252/DIG. 13; 424/70; 424/71

[58] Field of Search .................. 424/70, 71; 252/DIG. 13, 547, 548, 549, 550, 174.15

[56] References Cited

U.S. PATENT DOCUMENTS

| | | | |
|---|---|---|---|
| 4,176,176 | 11/1979 | Cella et al. | 424/70 |
| 4,312,813 | 1/1982 | Lindemann et al. | 424/70 |
| 4,704,272 | 11/1987 | On et al. | 424/70 |
| 4,734,277 | 3/1988 | Login | 424/70 |
| 4,741,855 | 5/1988 | Grote et al. | 252/142 |
| 4,765,975 | 8/1988 | Iovanni et al. | 424/70 |
| 4,788,006 | 11/1988 | Bolich et al. | 252/550 |
| 4,824,602 | 4/1989 | Juneja | 252/547 |
| 5,077,040 | 12/1991 | Bergmann et al. | 252/550 |
| 5,085,857 | 2/1992 | Reid et al. | 424/70 |
| 5,108,738 | 4/1992 | Halloran et al. | 252/174.15 |

Primary Examiner—Paul Lieberman
Assistant Examiner—M. Kopec
Attorney, Agent, or Firm—Stephan P. Williams

[57] ABSTRACT

A conditioning shampoo is provided in the form of an aqueous solution having a pH of about 5 to 6 and which includes, in percent by weight of the total composition:
(a) about 6 to 20% of at least one anionic surfactant;
(b) about 0.1 to about 5% of a dimethicone copolyol having an ethylene oxide/propylene oxide ratio of from about 70/30 to 80/20; and
(c) a conditioning component comprising a combination of (i) about 0.1 to 2% guar hydroxypropyltrimonium chloride, (ii) about 0.1 to 2% hydroxypropyl bis-isostearamidopropyldimonium chloride, (iii) about 0.05 to 1.5% of an aluminum salt of a mineral acid, and (iv) about 0.00001 to 0.01% of a fluoroquaternary.

6 Claims, No Drawings

CONDITIONING SHAMPOO

BACKGROUND OF THE INVENTION

1. Field of the Invention

This invention is concerned with shampoo compositions and, more particularly, with conditioning shampoos, that is, shampoos which have both the usual cleansing action and also a conditioning action. The use of such shampoos avoids the necessity for the separate use of a hair conditioner after the hair has been washed with a conventional shampoo having only a cleansing action.

2. Description of the Prior Art

While conditioning shampoo compositions are known, a disadvantage that arises with some of them is that on repeated use, there is a build-up of the conditioning ingredients on the hair so that the washed hair no longer feels pleasant to the user.

Conditioning shampoos have also be described and are commercially available which are said not to suffer from this disadvantage, that is, the build-up of conditioning agents. Such shampoo compositions are described, for example, in U.S. Pat. Nos. 4,704,272; 4,741,855; and 4,788,006.

SUMMARY OF THE INVENTION

An object of the present invention is to provide alternative conditioning shampoo compositions which are not subject to the significant build-up of conditioning ingredients on repeated use.

It has now been found that these requirements can be met by providing a conditioning shampoo in the form of an aqueous solution having a pH of about 5 to 6 which includes, in percent by weight of the total composition:

(a) about 6% to about 20% of at least one anionic surfactant;

(b) about 0.1% to about 5% of a dimethicone copolyol having an ethylene oxide/propylene oxide ratio of from about 60/40 to about 90/10; and (c) a conditioning component which includes, in combination, (i) about 0.1% to about 2% guar hydroxypropyltrimonium chloride, (ii) about 0.1% to about 2% hydroxypropyl bis-isostearamidopropyldimonium chloride, (iii) about 0.05% to about 1.5% of an aluminum salt, and (iv) about 0.00001% to about 0.01% of a fluoroquaternary. In certain preferred embodiments of the invention the composition also includes about 1% to about 5% of an amphoteric surfactant.

DESCRIPTION OF PREFERRED EMBODIMENTS

The shampoo composition according to the invention will contain cleansing agents which may be any of the anionic surfactants conventionally used in such compositions, these ingredients being used in the conventional proportions. The composition can, and usually will, contain further ingredients which provide particular desired characteristics or properties.

It is preferred that the composition should contain from about 6% to about 20%, more preferably about 12% to about 16% by weight of one or more anionic surfactants, such as TEA-lauryl sulfate, ammonium lauryl sulfate, sodium lauroyl sarcosinate, and the like. The cleansing agent component of the composition may also usefully include from about 1% to about 5% by weight of one or more amphoteric surfactants, such as cocamidopropyl betaine. (As used herein, ingredients are identified by their CTFA Adopted Names, i.e., the system of nomenclature for cosmetic ingredients promulgated by The Cosmetic, Toiletry, and Fragrance Association, Washington, D.C.)

According to the present invention, the conditioning shampoo composition includes from about 0.1% to about 5.0% to about 2% by weight of one or more dimethicone copolyols having an ethylene oxide/propylene oxide (EO/PO) ratio of from 60/40 to 90/10.

Dimethicone copolyol is a CTFA Adopted Name for polysiloxane polyether copolymers of the formula:

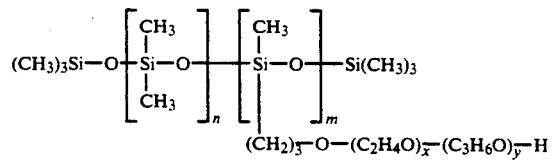

where n, m, x and y are integers. The dimethicone copolyols used according to the invention have values of x and y such that the ratio x:y, which is the EO/PO ratio, is from 60/40 to 90/10, with an EO/PO ratio of 70/30 to 80/20 being preferred. Preferred dimethicone copolyol contain from 60 to 140 $SiO_2$ units, that is, the sum of n and m is from 60 to 140.

Suitable dimethicone copolyols for use in the shampoo compositions according to the invention are available, for example, from Th. Goldschmidt AG, of Essen, Germany. A particularly preferred dimethicone copolyol having an EO/PO ratio of 77/23 is avialable as "Abil" B88184; this material contains about 60 $SiO_2$ units.

The conditioning component of the composition includes, in combination, (i) about 0.1% to about 2%, preferably about 0.2 to about 1%, guar hydroxypropyltrimonium chloride; (ii) about 0.1% to about 2%, preferably about 0.2% to about 0.5%, hydroxypropyl bis-isostearamidopropyldimonium chloride; (iii) about 0.05% to about 1.5%, preferably about 0.05% to about 0.5%, of an aluminum salt, with an aluminum salt of a mineral acid being preferred; and (iv) about 0.00001% to about 0.01%, preferably about 0.0001% to about 0.001%, of a fluoroquaternary. "Fluoroquaternary" is a coined name, not yet adopted by the CTFA, for cationic fluorosulfactants the use of which is hair conditioning is described in U.S. Pat. No. 4,765,975. A particularly preferred fluoroquaternary for use in the present invention is Zonyl FSC (du Pont) which has the formula $R_fCH_2CH_2SCH_2CH_2\text{-}N^+(CH_3)_3CH_3SO_4^{--}$ wherein $R_f$ is $F(CF_2CF_2)_{3-8}$ or FC-135 (3M Co.) which has the formula $RfSO_2NH_3H_6N^+(CH_3)_3I^-$ wherein Rf is $CnF_{2n+1}$ and n is about 8.

The conditioning shampoo compositions can also contain various adjuvants among which mention may be made of perfumes; colorants; preservatives; thickeners such as sodium chloride and cellulose gums such as hydroxypropyl methylcellulose; foam builders and stabilizers such as lauramide DEA, which helps the product develop a rich, creamy foam as well as providing additional conditioning benefits; pearling agents such as glycol distearate; pH adjusters such as citric acid or lactic acid; and chelating agents such as tetrasodium EDTA, to help overcome the effects of hard water.

In order that the invention may be more fully understood, the following examples, in which all percentages are by weight, are given by way of illustration only:

EXAMPLES 1-2

Two conditioning shampoo compositions were made up having the compositions set out in Table 1.

TABLE 1

| | % Active | |
|---|---|---|
| | Example 1 | Example 2 |
| TEA-Lauryl Sulfate | 7.0 | — |
| Ammonium Lauryl Sulfate | 5.0 | 8.0 |
| Sodium Lauroyl Sarcosinate | — | 8.0 |
| Cocamidopropyl Betaine | — | 2.0 |
| Dimethicone Copolyol (Abil 88184) | 0.75 | 0.75 |
| Guar Hydroxypropyltrimonium Chloride | 0.5 | 0.4 |
| Hydroxypropyl Bis-Isostearamido-propyldimonium Chloride | 0.35 | 0.35 |
| Aluminum Chloride | 0.1 | 0.1 |
| Fluoroquaternary (Zonyl FSC) | 0.0005 | 0.0005 |
| Sodium Chloride | 3.0 | 3.0 |
| Lauramide DEA | 3.0 | 3.0 |
| Citric Acid | 1.0 | 0.2 |
| Glycol Distearate | 0.4 | 0.4 |
| Hydroxypropyl Methylcellulose | 0.3 | 0.25 |
| Tetrasodium EDTA | 0.12 | 0.12 |
| Color, Perfume, Preservative, Water | to 100 | to 100 | processing of the products of Examples 1 and 2 is the conventional manner for shampoos.

The exemplary conditioning shampoo compositions provide excellent washing and overall conditioning, including ease of wet combing for the hair, without excessive build-up of conditioner over a period of use, comparable to the best products available in the market.

What is claimed is:

1. A conditioning shampoo in the form of an aqueous solution having a pH of about 5 to 6 and comprising, in percent by weight of the total composition in addition to water,
   (a) about 6% to about 20% of at least one anionic surfactant;
   (b) about 0.1% to about 5% of a water soluble dimethicone copolyol having an ethylene oxide/propylene oxide ratio of from about 70/30 to about 80/20; and
   (c) a conditioning component comprising, in combination, (i) about 0.1% to about 2% guar hydroxypropyltrimonium chloride, (ii) about 1% to about 2% hydroxypropyl bis-isostearamidopropyldimonium chloride, (iii) about 0.05% to about 1.5% of an aluminum salt of a mineral acid, and (iv) about 0.00001% to about 0.01% of a cationic fluorosurfactant.

2. A conditioning shampoo according to claim 1, which further comprises about 1% to about 5% of an amphoteric surfactant.

3. A conditioning shampoo according to claim 2 wherein the cationic fluorosurfactant is $R_fCH_2SCH_2CH_2N^+(CH_3)_3$ $CH_3SO_4^-$ wherein $R_f$ is $F(CF_2CF_2)_{3-8}$ or $R_fSO_2NHC_3H_6N^+(CH_3)_3I^-$ wherein $R_f$ is $C_nF_{2n+1}$ and n is about 8.

4. A conditioning shampoo according to claim 3 wherein the amphoteric surfactant is cocamidopropyl betaine.

5. A conditioning shampoo according to claim 1 comprising about 0.0001 to about 0.001% cationic fluorosurfactant.

6. A conditioning shampoo according to claim 3 comprising about 0.0005% cationic fluorosurfactant.

* * * * *

UNITED STATES PATENT AND TRADEMARK OFFICE
CERTIFICATE OF CORRECTION

PATENT NO. : 5,217,652
DATED : June 8, 1993
INVENTOR(S) : Carl F. Iovanni

It is certified that error appears in the above-identified patent and that said Letters Patent is hereby corrected as shown below:

Col. 4, line 13: delete "1%" and insert therefor -- 0.1% --.

Signed and Sealed this

Twelfth Day of April, 1994

BRUCE LEHMAN

*Commissioner of Patents and Trademarks*

*Attest:*

*Attesting Officer*